United States Patent [19]

Wagner et al.

[11] 4,369,162
[45] Jan. 18, 1983

[54] SILVER BASE CASTING ALLOY FOR DENTAL USE

[75] Inventors: Armin Wagner, Mine Hill, N.J.; Nils Harmsen, Garden City, N.Y.

[73] Assignee: W. C. Heraeus GmbH, Hanau am Main, Fed. Rep. of Germany

[21] Appl. No.: 298,630

[22] Filed: Sep. 2, 1981

[30] Foreign Application Priority Data

Nov. 6, 1980 [DE] Fed. Rep. of Germany ....... 3041894

[51] Int. Cl.³ .................... C22C 30/02; C22C 5/06; A61C 13/22
[52] U.S. Cl. .................... 420/503; 420/587; 420/502; 433/207
[58] Field of Search .................... 75/173 C, 134 N; 433/207, 222

[56] References Cited

U.S. PATENT DOCUMENTS 1,965,012  7/1934  Taylor .................... 75/173 C
3,667,936  6/1972  Katz .................... 75/134 N

*Primary Examiner*—L. Dewayne Rutledge
*Assistant Examiner*—David Hey
*Attorney, Agent, or Firm*—Frishauf, Holtz, Goodman & Woodward

[57] ABSTRACT

Silver base casting alloys for dental use which have a yellow color. They are useful for the manufacture of crowns, bridges and other dental prosthesis and such dental prosthesis are within the scope of the invention. The dental alloys consist essentially of 40–60% silver, 15–20% indium, 8–15% copper, 0.1–2% nickel, 0.1–2% zinc, from 0–10% gold and/or from 0–30% palladium. The total of gold and palladium content is between 10 and 30%.

10 Claims, No Drawings

SILVER BASE CASTING ALLOY FOR DENTAL USE

The present invention provides an improved casting alloy for dental use such as for the manufacture of crowns, bridges and other dental prosthesis. The casting alloy is a silver base alloy.

German Pat. No. 27 00 853 discloses a casting alloy for dental use composed of 20% gold, 18-22% palladium, 10-14% copper, 0.1-2% indium, 0.05-0.5% iridium and/or ruthenium with the remainder being silver. Gold base alloys are expensive.

It is the object of the present invention to provide a silver-base casting alloy for dental use which has a yellow color and which has the good qualities of the gold base casting alloys for dental use, which does not contain gold or which only contains a small amount of gold.

THE INVENTION

The present invention provides silver base casting alloys for dental use consisting essentially of between about 40 and 60% by weight silver, between about 15 and 20% indium, between about 8 and 15% copper, between about 0.1 and 2% nickel, between about 0.1 and 2% zinc, between 0 and about 10% gold, and between 0 and about 30% palladium, a total of the gold and palladium being between 10 and 30%, and dental prosthesis comprising said alloys.

The following alloys are preferred embodiments of the alloys of the present invention: 47-52% silver, 16-18% indium, 10-12% copper, 0.4-0.8% nickel, 0.4-0.8% zinc, 3-6% gold, 12-19% palladium with the total of gold and palladium from 15-25%.

Three illustrative alloys are specifically set forth and identified in Table 1. Alloy No. 2 is particularly preferred. The physical properties of these alloys are set forth in Table 2.

TABLE 1

| Alloy No. | Ag % | In % | Cu % | Ni % | Zn % | Au % | Pd % |
|---|---|---|---|---|---|---|---|
| 1 | 56 | 19 | 14 | 0.5 | 0.5 | 2 | 8 |
| 2 | 49 | 17 | 11 | 0.5 | 0.5 | 5 | 17 |
| 3 | 44 | 16 | 9 | 0.5 | 0.5 | 8 | 22 |

TABLE 2

| Alloy No. | Au + Pd % | HARDNESS (VICKERS 100g) Dead Annealed | Hardened | DENSITY g/cm$^3$ | MELTING RANGE °C. |
|---|---|---|---|---|---|
| 1 | 10 | 165 | 220 | 9.6 | 770-820 |
| 2 | 22 | 180 | 225 | 10.0 | 790-840 |
| 3 | 30 | 190 | 240 | 10.2 | 810-870 |

The present invention also provides dental prosthesis such as crowns, bridges, inlays, etc. which are advantageously and economically manufactured utilizing one of the silver base dental alloys disclosed herein. Such prosthesis includes prosthesis such as those disclosed in U.S. Pat. Nos. 2,948,963 and 4,124,380 which are incorporated by this reference.

The silver base dental casting alloys of the present invention are readily processed. They are easily melted and cast. The finished castings take a very good polish. The alloys exhibit good cold working characteristics. They are of a pleasing yellow color depending upon the specific alloy content.

The alloys of the present invention have been subject to corrosion testing in the presence of sodium polysulfide. They exhibit good resistance to tarnishing. When utilized in the human mouth, no signs of corrosion were observed even after a period of four weeks.

The gold color casting alloys for dental use of the present invention have a relatively low density and therefore a cost advantage when compared with known yellow and white gold base casting alloys. They also have a cost advantage when compared with white palladium-silver base casting alloys.

The casting alloys of the present invention have a relatively low melting point range which provides the further advantage that in the dental casting operation, embedding (matrices) which are bonded with gypsum and therefore relatively inexpensive, may be used in place of the more expensive embedding means bonded with phosphates which are used with higher melting alloys. Gypsum bonded embedding means are also easier to work with than the phosphate bonded embedding means.

Various changes and modifications may be made within the scope of the inventive concept.

We claim:

1. A silver base casting alloy for dental use consisting essentially of between about 40 and 60% by weight silver, between about 15 and 20% indium, between about 8 and 15% copper, between about 0.1 and 2% nickel, between about 0.1 and 2% zinc, up to 10% gold and up to 30% palladium, with the total gold and palladium content being between about 10 and 30%.

2. The casting alloy of claim 1 consisting essentially of between about 47 and 52% by weight silver, between about 16 and 18% indium, between about 10 and 12% copper, between about 0.4 and 0.8% nickel, between about 0.4 and 0.8% zinc, between about 3 and 6% gold and between about 12 and 19% palladium, with the total gold and palladium content being between about 15 and 25%.

3. The casting alloy of claim 2 consisting essentially of 49% silver, 17% indium, 11% copper, 0.5% nickel, 0.5% zinc, 5% gold and 17% palladium.

4. The casting alloy of claim 1 consisting essentially of 56% silver, 19% indium, 14% copper, 0.5% nickel, 0.5% zinc, 2% gold and 8% palladium.

5. The casting alloy of claim 1 consisting essentially of 44% silver, 16% indium, 9% copper, 0.5% nickel, 0.5% zinc, 8% gold and 22% palladium.

6. A dental prosthesis comprising a dental alloy consisting essentially of the casting alloy of claim 1.

7. A dental prosthesis comprising a dental alloy consisting essentially of the casting alloy of claim 2.

8. A dental prosthesis comprising a dental alloy consisting essentially of the casting alloy of claim 3.

9. A dental prosthesis comprising a dental alloy consisting essentially of the casting alloy of claim 4.

10. A dental prosthesis comprising a dental alloy consisting essentially of the casting alloy of claim 5.

* * * * *